United States Patent
Dickinson et al.

(10) Patent No.: US 11,659,343 B2
(45) Date of Patent: May 23, 2023

(54) HEARING ENHANCEMENT AND PROTECTION DEVICE

(71) Applicant: SoundTrack Outdoors, LLC, Mt. Juliet, TN (US)

(72) Inventors: William Dickinson, Brentwood, TN (US); David Gnewikow, Mt. Juliet, TN (US)

( * ) Notice: Subject to any disclaimer, the term of this patent is extended or adjusted under 35 U.S.C. 154(b) by 143 days.

(21) Appl. No.: 16/901,975

(22) Filed: Jun. 15, 2020

(65) Prior Publication Data

US 2020/0396552 A1    Dec. 17, 2020

Related U.S. Application Data

(60) Provisional application No. 62/860,867, filed on Jun. 13, 2019.

(51) Int. Cl.
*H04R 25/00* (2006.01)
*H04R 1/10* (2006.01)

(52) U.S. Cl.
CPC ........... *H04R 25/65* (2013.01); *H04R 1/1083* (2013.01); *H04R 25/43* (2013.01); *H04R 25/505* (2013.01); *H04R 25/604* (2013.01); *H04R 2225/0213* (2019.05); *H04R 2225/0216* (2019.05)

(58) Field of Classification Search
CPC .......... H04R 1/1083; H04R 2225/0213; H04R 2225/0216; H04R 25/43; H04R 25/505; H04R 25/604; H04R 25/65; H04R 1/1016; H04R 2225/025; H04R 2410/05; H04R 2430/03; H04R 25/356; H04R 25/453; H04R 25/606; H04R 25/607; H04R 3/02
USPC ........................................................ 381/322
See application file for complete search history.

(56) References Cited

U.S. PATENT DOCUMENTS

| | | |
|---|---|---|
| 6,732,073 B1 | 5/2004 | Kluender et al. |
| 6,885,752 B1 | 4/2005 | Chabries et al. |
| 8,150,044 B2 | 4/2012 | Goldstein et al. |
| 8,229,740 B2 | 7/2012 | Nordholm et al. |
| 9,180,055 B2 | 11/2015 | Kirsch et al. |

(Continued)

FOREIGN PATENT DOCUMENTS

| | | |
|---|---|---|
| AU | 2014349101 B2 | 6/2017 |
| KR | 1020170059796 A | 5/2017 |
| WO | 2017027186 A1 | 2/2017 |

OTHER PUBLICATIONS

PCT/US2020/037884 International Search Report and Written Opinion, dated Sep. 29, 2020, 13 pages.

*Primary Examiner* — Phylesha Dabney
(74) *Attorney, Agent, or Firm* — Waller Lansden Dortch & Davis, LLP; Blake M. Bernard (57) ABSTRACT

A listening device is disclosed for positioning in an ear canal of a user to process an environmental sound signal. The device can include an earpiece positionable in the ear canal of the user. A microphone can be positioned on the earpiece for receiving the environmental sound signal when the earpiece is positioned in the user's ear canal. A sound processing unit can be electrically coupled with the microphone, the sound processing unit programmed to produce a processed sound signal by identifying a target sound signature within the environmental sound signal received from the microphone, and modifying the identified target sound signature within the processed sound signal. A speaker can be electrically coupled to the sound processing unit, the speaker configured to project the processed sound signal as audible sound.

20 Claims, 7 Drawing Sheets

(56) References Cited

U.S. PATENT DOCUMENTS

| | | |
|---|---|---|
| 9,198,800 B2 | 12/2015 | Killion et al. |
| 9,463,118 B2 | 10/2016 | Meegan et al. |
| 2006/0233411 A1 | 10/2006 | Utigard |
| 2014/0254842 A1 | 9/2014 | Smith et al. |

TABLE G-16 - PERMISSIBLE NOISE EXPOSURES (1)

| Duration per day, hours | Sound level dBA slow response |
|---|---|
| 8 | 90 |
| 6 | 92 |
| 4 | 95 |
| 3 | 97 |
| 2 | 100 |
| 1 1/2 | 102 |
| 1 | 105 |
| 1/2 | 110 |
| 1/4 or less | 115 |

Footnote(1) When the daily noise exposure is composed of two or more periods of noise exposure of different levels, their combined effect should be considered, rather than the individual effect of each. If the sum of the following fractions: $C(1)/T(1) + C(2)/T(2)$ $C(n)/T(n)$ exceeds unity, then, the mixed exposure should be considered to exceed the limit value. Cn indicates the total time of exposure at a specified noise level, and Tn indicates the total time of exposure permitted at that level. Exposure to impulsive or impact noise should not exceed 140 dB peak sound pressure level.

HEARING ENHANCEMENT AND PROTECTION DEVICE

CROSS REFERENCES TO RELATED APPLICATIONS

This application claims the benefit of U.S. Provisional Application No. 62/860,867 filed on Jun. 13, 2019 and entitled "HEARING ENHANCEMENT AND PROTECTION DEVICE," which is incorporated by reference herein in its entirety.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present disclosure relates generally to hearing enhancement and protection devices for hunters and firearms enthusiasts. Hunters and firearm enthusiasts are often faced with the dilemma of choosing between protecting their ears from harmful sounds, such as that of a firearm discharge, and hearing beneficial sounds such as a nearby animal being hunted. Sound pressure levels created from the discharge of a firearm can reach dangerous levels of greater than 150 dB SPL, thus creating the potential for permanent damage to a hunter's hearing. The Occupational Safety and Health Administration (OSHA) 1910.95—occupational noise exposure standard specifies that impulse noises are considered unsafe and hearing protection required, when the peak level exceeds 140-dB SPL. As such, hearing protection should be worn during hunting activities or other activities where firearms are discharged.

However, traditional hearing protection devices (passive earmuffs, earplugs, etc.) limit the wearer's ability to hear conversation and environmental sounds. Decreased hearing sensitivity while wearing hearing protection can create problems communicating with other individuals around the shooter causing frustration and potential safety hazards if warnings and instructions cannot be heard clearly. With respect to hunters, accurately hearing environmental sounds can be critical to success. For many forms of hunting, the hunter needs to hear vocalizations and movement sounds of approaching game. Acute hearing is often required to determine the location of the game animal. Hunting strategies for some animals (e.g. turkey, elk) are based almost exclusively around initially hearing the game animal vocalizations. Once the game animal is heard, the hunter then often uses a combination of physically moving into a position to intercept the prey along with calling to bring the animal into range.

Figure 1:
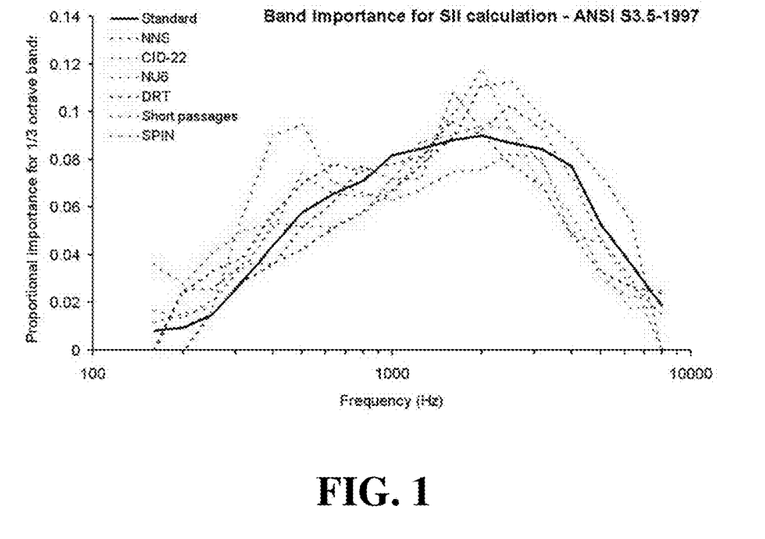
FIG. 1 is a plot of the relative importance of various frequency bandwidths relative to the calculation of the speech intelligibility index.

The use of electronic amplification targeted at specific frequencies is used in traditional hearing aids. Hearing aids have been used for many years to help individuals with hearing impairments to better hear human speech frequencies. Human speech sounds range from 200-Hertz (Hz) to 6000-Hz, with primary energy and density of importance in the 1000-2500-Hz range. FIG. 1 shows the band importance functions of various stimuli used for assessing speech understanding. The accepted protocol for fitting hearing aids requires the device's frequency response to be adjusted to a prescription. The prescription is a formula based upon the degree of hearing loss and spectral composition of human speech. Hearing aid amplification parameters (gain and frequency response) are adjusted to allow the individual to better detect the most important frequencies of the human voice, thus improving awareness of voices, word recognition and overall speech understanding. However, typical hearing aid devices do not differentiate between different types of speech, or specific acoustical signatures for a particular person or speech within these frequency ranges. As such all types of speech or sounds within these frequency ranges can be amplified in conventional hearing aids.

Calling game takes different forms depending on the hunting scenario and creates yet another hunting/hearing dilemma. In human speaking, hearing is required to monitor the level of one's voice and accurately produce speech sounds. Similarly, hearing on the part of the hunter is required to accurately reproduce game sounds when calling. Thus, the use of many types of hearing protection adversely affects the hunter's ability to accurately produce the desired sound due to decreased hearing sensitivity and altered frequency response. Furthermore, some types of calling (e.g. duck, goose) must be produced at loud levels to allow the animal to hear or respond to the calling. Thus, game calling for hunters requires good hearing, yet, like the report of the gun, can reach potentially harmful levels.

The issues noted above with conventional hearing protection devices often cause hunters and firearm enthusiasts to avoid using hearing protection all together, such hearing protection otherwise making such distant sounds unrecognizable, which can lead to long term hearing damage for the hunter and firearm enthusiasts after repeated exposure to harmful sounds. Some hunters will alternatively remove and reapply hearing protection when the hunter alternates from trying to hear an animal and preparing to fire, which is cumbersome at best and in many instances in the heat of the moment a hunter may forget to replace the hearing protection before firing the weapon, which could let to hearing damage.

What is needed then are improvements in hearing enhancement and protection devices, particularly for hunters and other firearms enthusiasts.

BRIEF SUMMARY

This Brief Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

One aspect of the disclosure is a hearing device for positioning in an ear canal of a user to process an environmental sound. The hearing device can include an earpiece, at least a portion of the earpiece shaped to occlude the ear canal of the user when the portion of the earpiece is positioned in the ear canal of the user. A microphone can be positioned on the earpiece for receiving the environmental sound when the earpiece is positioned in the user's ear canal. A sound processing unit can be electrically coupled to the microphone, the sound processing unit programmed to produce a processed sound signal by identifying a target sound signature within the environmental sound received from the microphone, and modifying the target sound signature within the processed sound signal. In some embodiments, modifying the identified target sound signature can include amplifying the identified target sound signature if the identified target sound signature has an amplitude below a predetermined amplitude threshold, and/or attenuating the identified target sound signature if the amplitude of the identified target sound signature is above a predetermined amplitude maximum. A speaker can be electrically coupled to the sound processing unit, the speaker configured to project the processed sound signal as audible sound. As such, the device can identify a target sound signature within a received environmental sound, and either amplify or attenuate that target sound based on the amplitude of that sound.

In some embodiments, substantially all background sound signatures within the environmental sound signal can be passed through and included in the processed sound signal in an unaltered state, or can be flat attenuated to provide compensation for hearing loss. As such, a user can generally hear the majority of the environmental sound signal via the processed sound signal as if the user was not wearing any hearing protection device. Target sounds of interest can be amplified or attenuated as needed to allow the user to better hear and identify such target sounds.

A sound processing unit programmed with such functionality can be of particular benefit to a hunter in attempting to call game while hunting, as the hunter will want to hear both a call made by the game, as well as the hunter's own simulated game call from a calling device. The call from the game and the simulated call made by the hunter are intended to have similar sound signatures or frequency spectrums. However, it can be desirable for a far off call from the game itself to be amplified, while a loud simulated call made by the hunter close to the hunter's ear to be attenuated. The sound processing unit differentiating between a target sound signature based on an amplitude of the target sound signature can allow the sound processing unit to differentiate between these two types of game calls having similar sound signatures or spectral frequencies, which can allow the two sounds to be processed differently by the sound processing unit. Such a system can help enhance a user's hearing of both the call originating from the game and the simulated call made by the hunter, while providing adequate hearing protection in relation to these two different sounds.

Another aspect of the present disclosure is a method of processing an environmental sound signal; the method including the steps of: providing a listening device having an earpiece, a microphone positioned on the earpiece, a sound processing unit communicated with the microphone, and a speaker communicated with the sound processing unit; placing the earpiece in the ear of a user with at least a portion of the earpiece positioned within the ear canal of the user; receiving with the microphone the environmental sound signal; processing the environmental sound signal with the sound processing unit to: identify a target sound signature within the environmental sound signal; amplify the at least one identified target sound signature if the identified target sound signature has an amplitude below a predetermined amplitude threshold; and attenuate the at least one identified target sound signature if the amplitude of the identified target sound signature is above a predetermined target sound amplitude maximum; and projecting the processed sound signal as an audible sound through a speaker on the ear piece into the ear canal of the user.

In some embodiments, the sound processing unit can also be programmed to identify undesirable sound signatures, such as gunshots, and attenuate such undesirable sound signatures in producing the processed sound signal that is transmitted via the speaker to a user's ear.

Numerous other objects, advantages and features of the present disclosure will be readily apparent to those of skill in the art upon a review of the following drawings and description of a preferred embodiment.

DETAILED DESCRIPTION

While the making and using of various embodiments of the present invention are discussed in detail below, it should be appreciated that the present invention provides many applicable inventive concepts that are embodied in a wide variety of specific contexts. The specific embodiments discussed herein are merely illustrative of specific ways to make and use the invention and do not delimit the scope of the invention. Those of ordinary skill in the art will recognize numerous equivalents to the specific apparatus and methods described herein. Such equivalents are considered to be within the scope of this invention and are covered by the claims.

In the drawings, not all reference numbers are included in each drawing, for the sake of clarity. In addition, positional terms such as "upper," "lower," "side," "top," "bottom," etc. refer to the apparatus when in the orientation shown in the drawing. A person of skill in the art will recognize that the apparatus can assume different orientations when in use.

Figure 7:
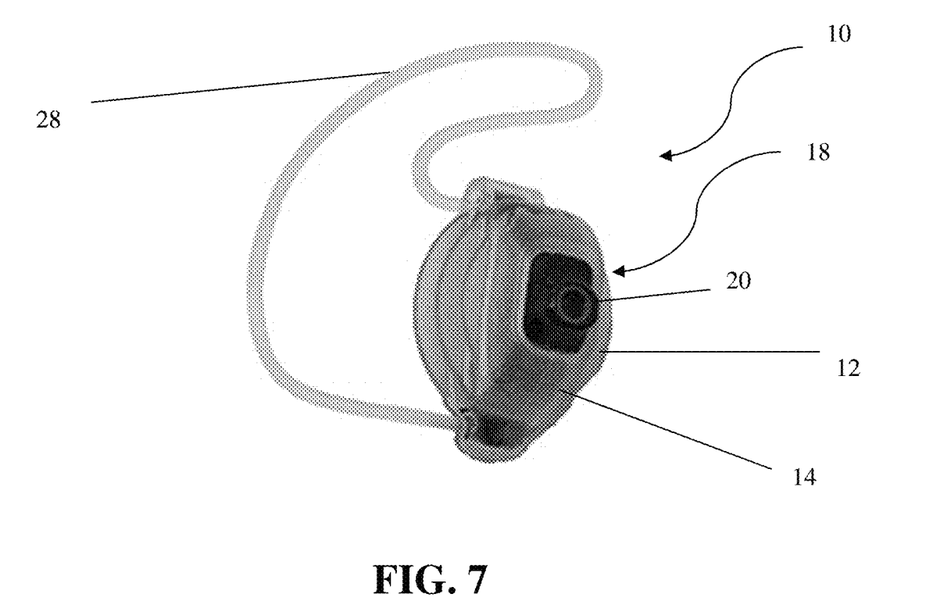
FIG. 7 is a perspective view of a first embodiment of a hearing device of the present disclosure.
Figure 7A:
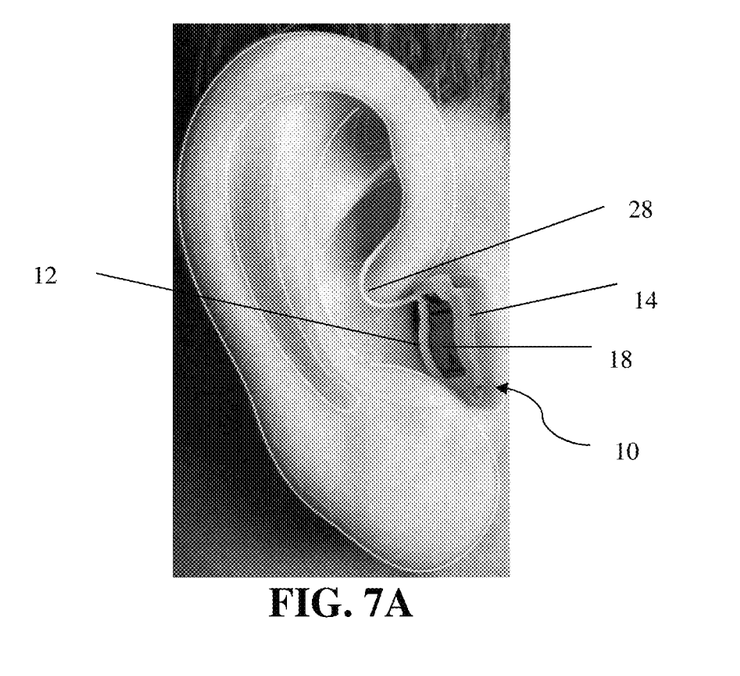
FIG. 7A is a perspective view of the hearing device of FIG. 7 inserted into the ear canal of a user.
Figure 8:
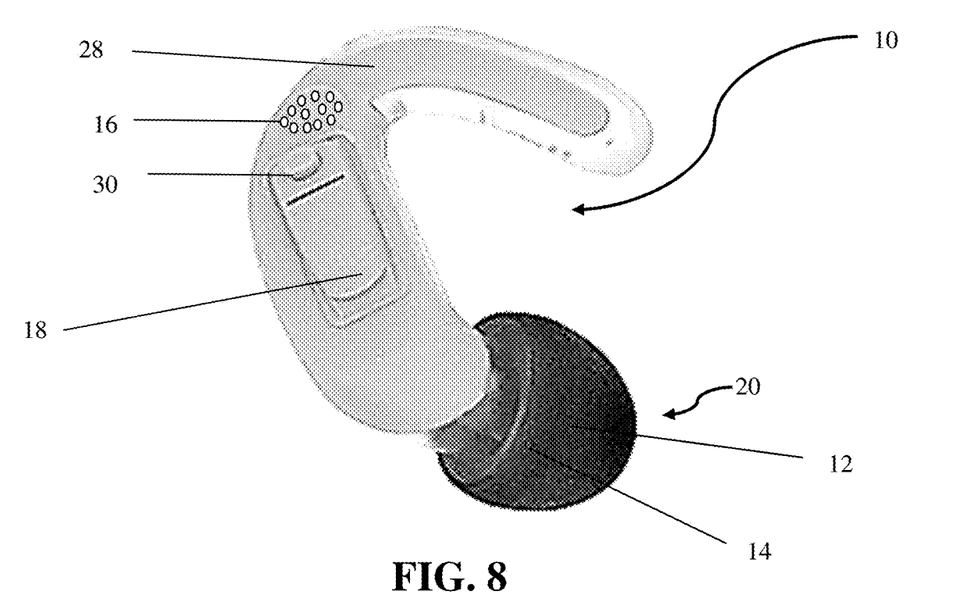
FIG. 8 is a perspective view of another embodiment of a hearing device of the present disclosure.
Figure 8A:
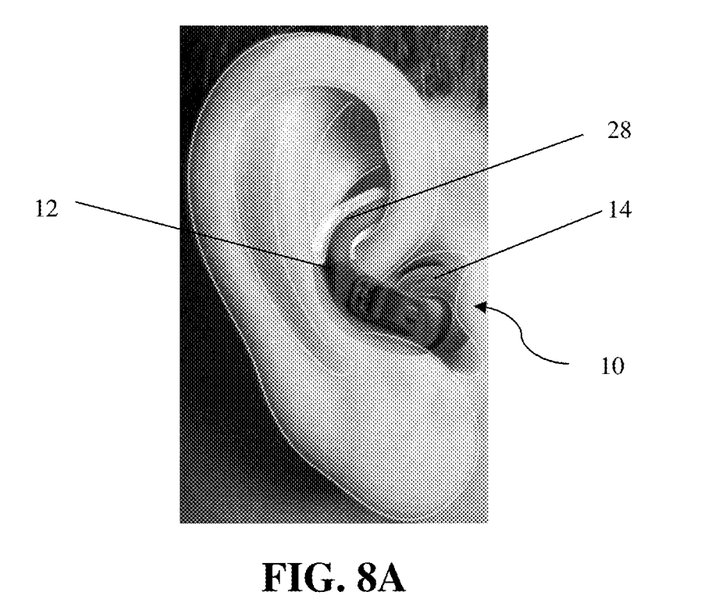
FIG. 8A is a perspective view of the hearing device of FIG. 8 inserted into the ear canal of a user.
Figure 9:
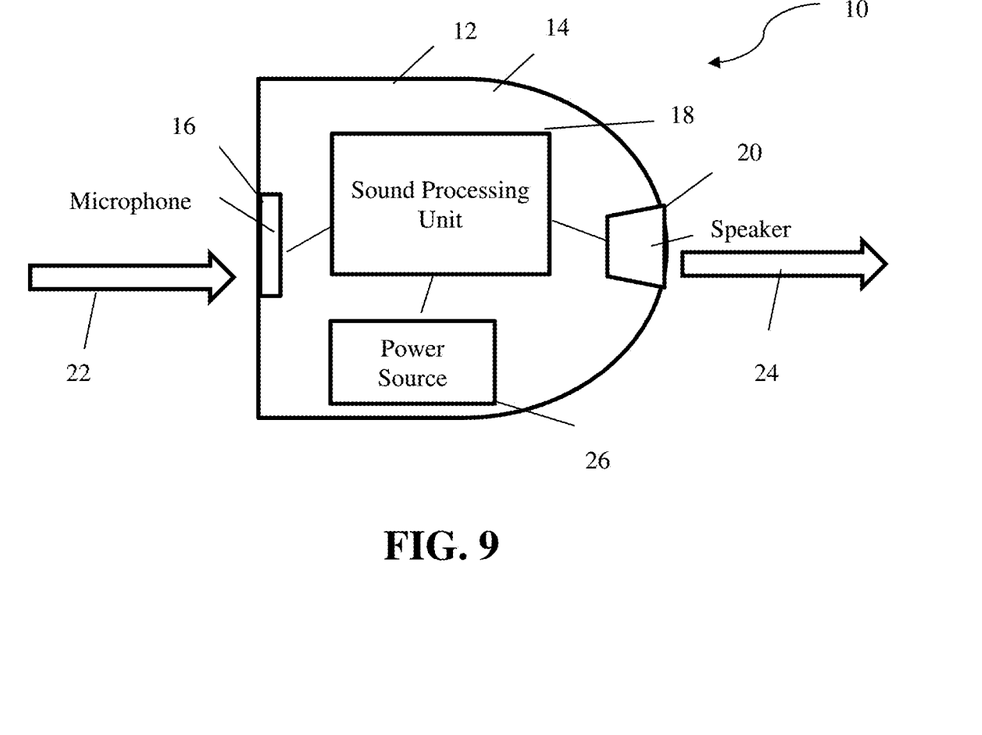
FIG. 9 is a schematic view of yet another embodiment of a hearing device of the present disclosure.

Referring to FIGS. 7-9, a hearing device 10 is disclosed herein for positioning in an ear canal of a user to process an environmental sound 22. The hearing device 10 can include an earpiece 12, at least a portion 14 of the earpiece 12 shaped to occlude the ear canal of the user when the at least a portion 14 of the earpiece 12 is positioned in the ear of the user. A microphone 16 can be positioned on the earpiece 12 for receiving the environmental sound 22 when the at least a portion 14 of the earpiece 12 is positioned in the user's ear. A sound processing unit 18 can be electrically coupled to the microphone 16. The sound processing unit 18 can be programmed to produce a processed sound signal 24 by identifying a target sound signature within the environmental sound 22 received from the microphone 16, and modifying the target sound signature as desired. In some embodiments, modifying the target sound signature can include amplifying the identified target sound signature if the identified target sound signature has an amplitude below a predetermined target sound amplitude threshold, and attenuating the identified target sound signature if the amplitude of the identified target sound signature is above a predetermined target sound amplitude maximum. A speaker 20 can be electrically coupled to the sound processing unit 18, the speaker 20 configured to project the processed sound signal 24 as audible sound. As such, the device 10 can identify a target sound signature within a received environmental sound 22, and either amplify or attenuate the target sound signature based on the amplitude of that sound. The hearing device 10 can include a power source 26, such as a battery, which can provide power to the sound processing unit 18 and/or other components of the hearing device 10 during use. In some embodiments, as shown in FIGS. 7-8, the earpiece 12 can include an ear connection piece 28 which can be at least partially received around a user's outer ear to help secure the device 10 to the user's ear with the at least a portion 14 of the earpiece 12 positioned within the ear canal of the user.

Figure 10:
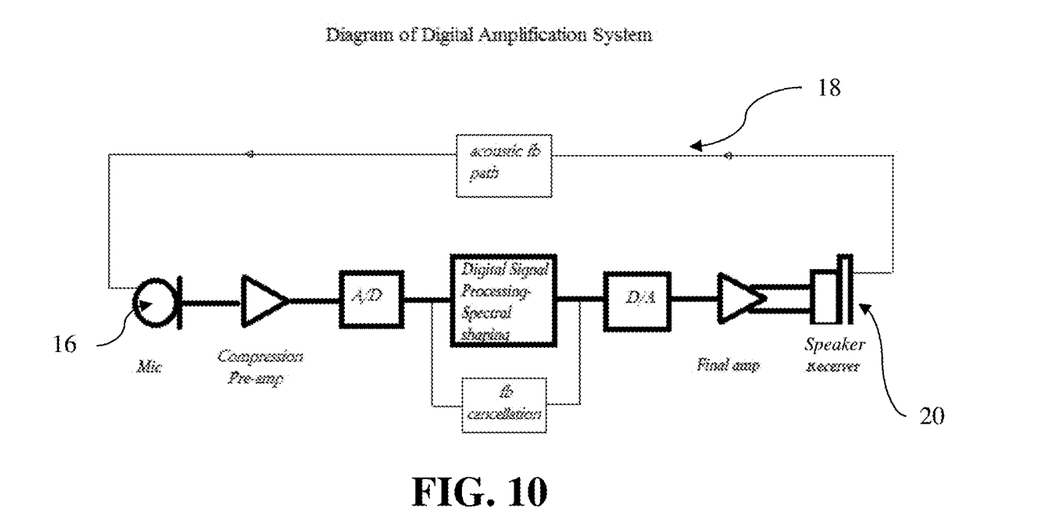
FIG. 10 is a schematic view of an embodiment of a sound processing unit of the present disclosure.

In some embodiments, as shown in FIG. 10, the sound processing unit 18 can receive the environmental sound signal from the microphone 16 as an audio signal. The sound processing unit 18 can include an audio to digital converter that can convert the environmental sound signal to a digital signal. A digital processor can digitally process the environmental sound signal as described herein to create the processed sound signal. The processed sound signal can be converted back to an audio signal via a digital to audio converter, and the audio signal can be projected by the speaker 20.

Figure 2:
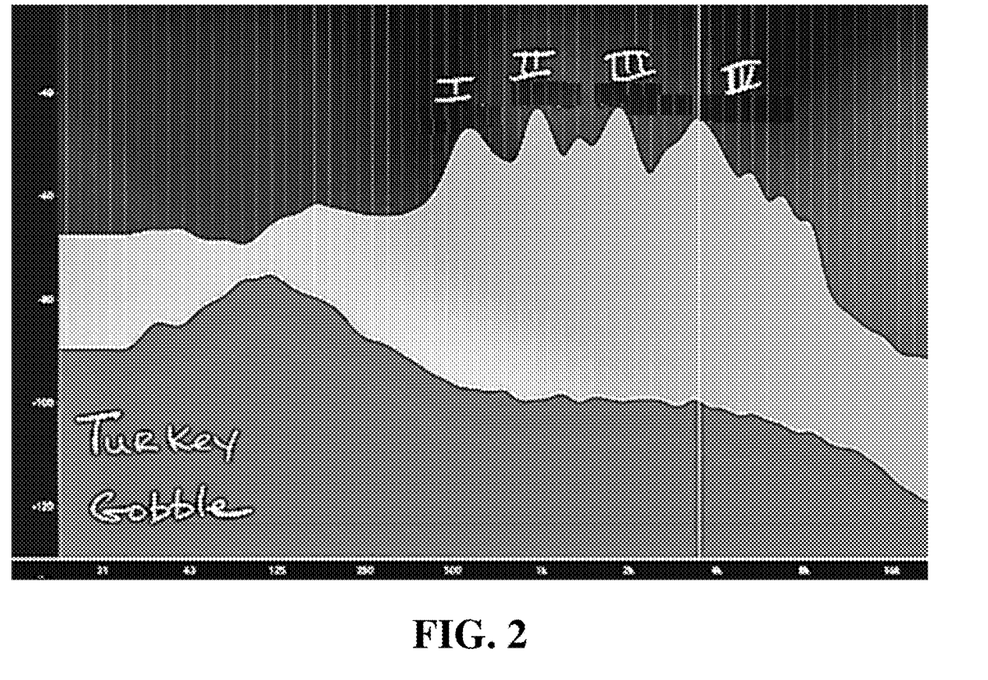
FIG. 2 is a plot of a frequency spectrum corresponding to a turkey gobble.

Like human speech, game animal sounds have unique spectral characteristics or "sound signatures." For example, male turkeys produce vocalizations commonly known as "gobbles." Gobbles have a unique frequency spectrum with a first energy peak between about 500-600-Hz, a second energy peak between about 900-1100 Hz, a third energy peak between about 1800-2000 Hz, and a fourth energy peak between about 3200-3400 Hz. FIG. 2 shows a representative plot of a frequency spectrum for a turkey gobble. In some embodiments the target sound signature which the sound processing unit 18 is programmed to identify can have a frequency spectrum which corresponds to a turkey gobble.

Figure 3:
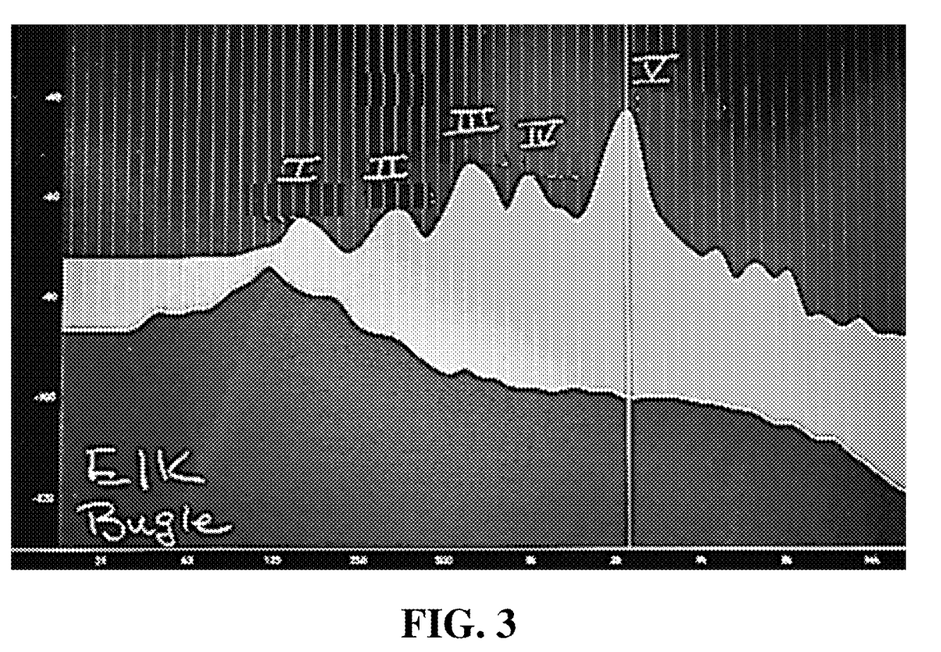
FIG. 3 is a plot of a frequency spectrum corresponding to an elk bugle.
Figure 4:
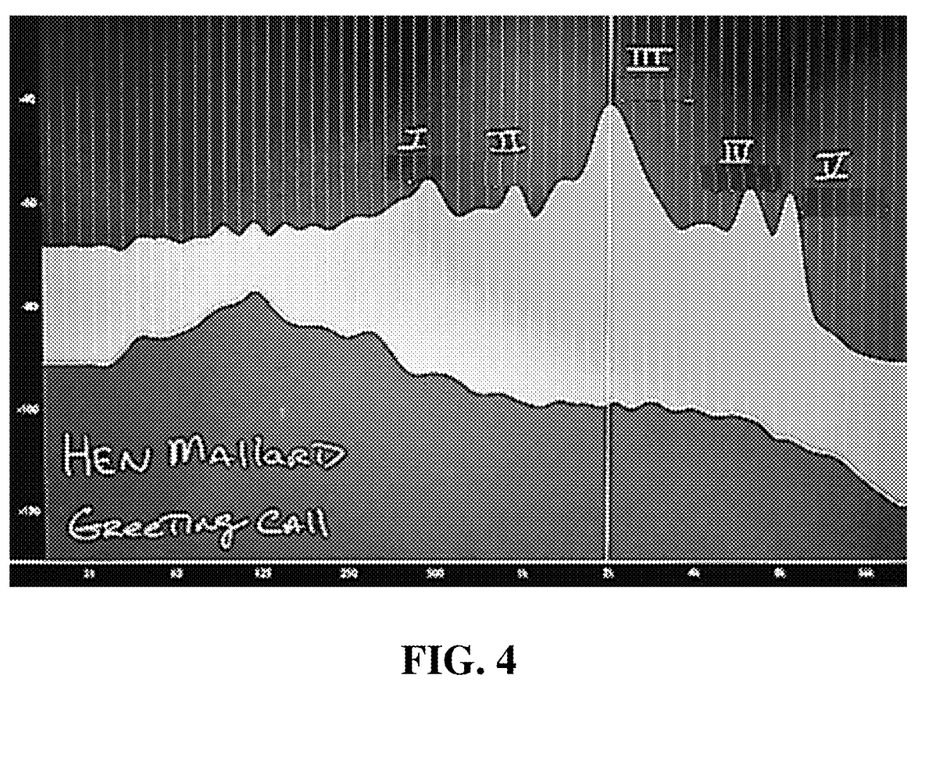
FIG. 4 is a plot of a frequency spectrum corresponding to a mallard greeting call.

Male elk create a vocalization known as a "bugle." Like the gobble, bugles have a unique sound signature comprised of several secondary lower frequency spectral peaks at between about 100-300 Hz, between about 300-400 Hz, between about 500-700 Hz, and between about 850-1050 Hz, respectively, with a primary energy peak at between about 2000-2500 Hz. FIG. 3 shows a representative plot of a frequency spectrum of an exemplary Elk Bugle. In some embodiments, the target sound signature can have a frequency spectrum which corresponds to an elk bugle.

Mallards or ducks, and particularly female mallards or ducks, can create vocalizations that are used as greeting or mating calls. The mallard greeting call can have a unique sound signature including several secondary lower frequency spectral peaks at between about 350-550 Hz, between about 900-1100 Hz, between about 5800-6200 Hz, and between about 8300-8700 Hz, respectively, with a primary energy peak at between about 1800-2000 Hz. FIG. 3 shows a representative plot of a frequency spectrum of an exemplary mallard greeting call. In some embodiments the target sound signature can have a frequency spectrum which corresponds to a mallard greeting call.

Any number of other animal species produce sounds with specific and individualized spectral frequency signatures, including vocalizations, or sounds made by movement (wings flapping, leaves crunching under hoof, etc.). Such target sound signatures can include Fourier transforms, frequency spectrums, or waveforms which can be programmed into the sound processing unit 18 via a stored memory device and which can be used to identify the target sound signature from the environmental sound 22. It will be understood by one of skill in the art that while certain examples have been provided herein, the target sound signature that the sound processing unit 18 is programmed to identify can be varied in different applications depending on the game, animal, or target sound of interest. In some embodiments, the hearing device 10 can include a switch connectable to the sound processing unit 18, the switch operable to adjust the target sound signature that the sound processing unit 18 is programmed to identify and/or amplify. In FIG. 8, the switch 30 is shown as a push button that can be sequentially pushed or toggled to selectively alternate the sound processing unit between different modes wherein different target sound signatures are identified and modified. For instance, in some embodiments, the hearing device 10 and the sound processing unit 18 can alternate between identifying vocalizations for turkey, elk, mallards, water fowl, deer, or upland game, the user able to selectively alternate which animal sound the sound processing unit 18 is trying to identify and amplify depending on the type of game the user or hunter is pursuing in a given hunt. This allows a user to use a single hearing device to enhance hearing when hunting different types of game.

While hunting applications are discussed in detail herein, the hearing and listening device disclosed herein can be used for many different applications which may have desired target sounds which the user is keen on hearing. Such applications can include bird watching, musical or concert settings, industrial applications, farming applications, medical settings, etc.

The current invention incorporates an adjustable frequency response to apply gain/amplification to accentuate a target spectral sound signature corresponding to a target sound. By applying amplification thusly, the target sound signature produced by the target animal can be accentuated, while signals of lesser interest to the hunter receive less emphasis. This process increases the hunter's ability to detect and locate the specific animal or target he or she is pursuing.

In some embodiments, sounds other than the target sound signature can be attenuated to reduce the effect of any noise being processed along with the target sound signature. Such a system can provide an even stronger emphasis on the target sound signature being amplified as other noises are attenuated or reduced. In other embodiments, such sound or background noise can simply be passed through the sound processing unit without being amplified or attenuated. Such a system can allow other sounds like speech, nature sounds (running water, wind, non-target animal sounds, etc.), far off gunshots, etc. or other sounds which would not produce hearing damage, and which would normally be heard without hearing protection, to pass through the sound processing unit 18 without being processed. In such embodiments, the target sound signature from an animal or target of interest would still be emphasized or amplified within the processing sound signal 24 produced by the sound processing unit 18 while other non-harmful sounds could be heard by the user. Such an arrangement allows the user to hear everything they otherwise would if they were not wearing a hearing or listening device. However, any background sound signature having an amplitude above a predetermined maximum background amplitude could be attenuated such that the background sound signature is passed through as part of the processed sound signal 24 at a safe level.

Active or electronic hearing protection uses a microphone 16, sound processing unit 18 and a speaker 20 (receiver) to deliver a processed sound signal 24 to the wearer. The processed sound signal 24 outputted from the system can be regulated so that a high-level, impulse sound, such as a gunshot, is limited to a pre-determined, safe level. The sound processing unit 18 can be programmed to identify an undesirable sound signature, such as a firing of a gun, which can be above a predetermined amplitude or sound pressure level that could cause damage to a user's ear and/or hearing. In some embodiments, the undesirable sound signature can be attenuated to a safe level by the sound processing unit 18. In other embodiments, the undesirable sound signature can be filtered out by the sound processing unit all together, such that the undesirable sound signature can be attenuated by the hearing protection capabilities of the earpiece 12. The earpiece 12 can be made from a foam, gel, rubber or other suitable material that can form a seal within the user's ear to effectively attenuate sound directed toward the user's ear. In such embodiments, the portion of the earpiece 12 positioned in the user's ear canal can be said to fully occlude the ear canal such that any sound entering the ear canal can be attenuated by the earpiece itself, similar to conventional earplugs. Thus, for quieter target or desirable sounds, there is amplification to maintain hearing and communication; however, when a loud impulse sound occurs, the amplification shuts down. The undesirable sound is attenuated by the protective ability of the device 10 based upon the degree to which the physical structure (the earpiece 12) of the device 10 attenuates sound delivered to the tympanic membrane.

However, one aspect of the current sound processing technique is that for impulse sounds or other undesirable or harmful sounds which are picked up by the microphone, the undesirable or harmful sound signature can still be produced in the processed sound signal 24 which is delivered to the user's ear, such that the user can hear a fresh, clear sound signature mimicking the harmful or undesirable sound signature such that the user can still safely hear the undesirable or harmful sound signature and better ascertain the direction or subtleties in the sound signature of the undesirable sound signature, which provides an advantage over prior art devices such as conventional earplugs that simply muffle the harmful sound with the earpiece, which can distort the sound and tone of the harmful sound.

The hearing devices of the present disclosure incorporates an active, electronic amplification system as described above. When input environmental sounds 22 are at safe levels, the invention amplifies them based on the pre-programmed, target specific algorithm described above. When an undesirable or harmful sound signature associated with an impulse noise activates the limiter, gain is immediately reduced to zero, reducing the experienced sound pressure level of the signal in the wearer's ear. In some embodiments, the sound processing unit 18 can be programmed to reduce the gain of any sound signature, other than the target sound signature, that has an amplitude above a predetermined safe amplitude to zero. In still other embodiments, the sound processing unit 18 can be programmed to attenuate any sound other than the target sound signature, even those not at a harmful amplitude, to further enhance the amplification of the target sound signature by reducing environmental noise.

Figure 6:
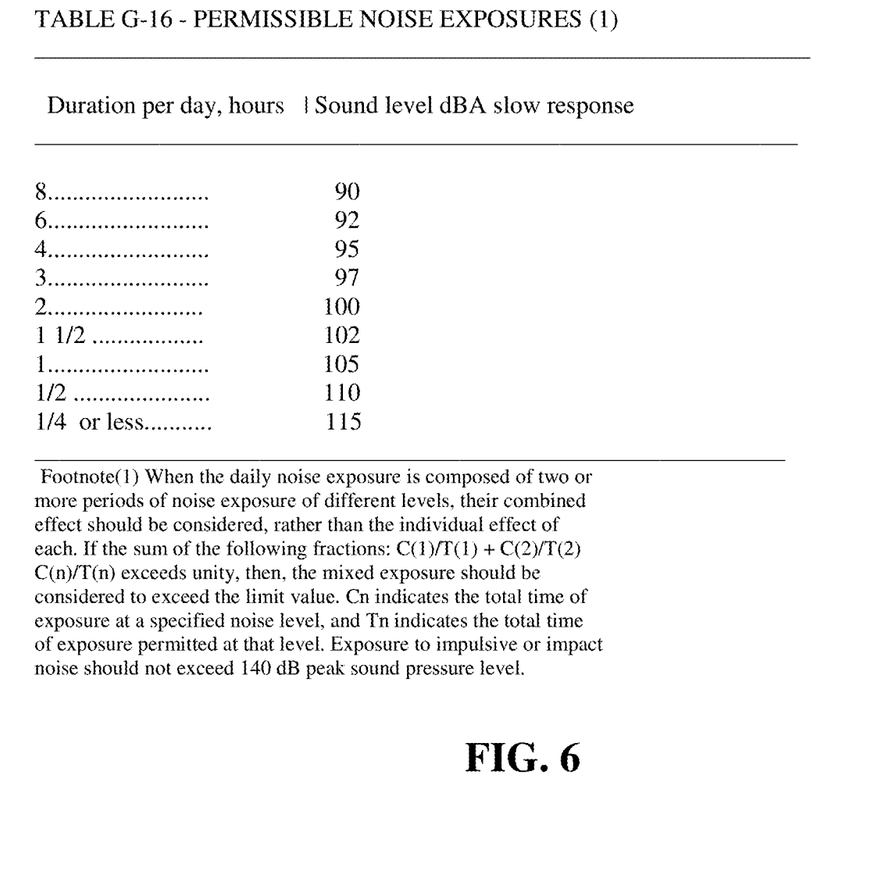
FIG. 6 is a table of permissible noise exposures based on exposure time and decibel levels as established by the Occupational Safety and Health Administration.

Waterfowl calls can routinely reach sound pressure levels in excess of 110 dB SPL. While this level does not exceed the OSHA minimum for an impulse noise, OSHA requires that workers exposed to more continuous loud signals use hearing protection. Table G-16, shown in FIG. 6, from the OSHA noise standard guidelines requires hearing protection when an individual is exposed to signal of 110 dB SPL (A-weighted) for 30 minutes during the day, and if there is any exposure to signals of 115 dB SPL (A-weighted).

Simulated animal call levels made by a hunter routinely fall into this range. Furthermore, taking into account that in a hunting scenario, multiple hunters may be calling simultaneously in a closed-in space (hunting blind), an argument can be made that hunters require protection during calling alone to prevent Noise-Induced Hearing Loss (NIHL). In addition to limiting sudden loud sounds, the current invention compresses longer-term signals above a pre-determined amplitude threshold, thus reducing the sound pressure levels experienced during loud calling by the user/wearer.

Figure 5:
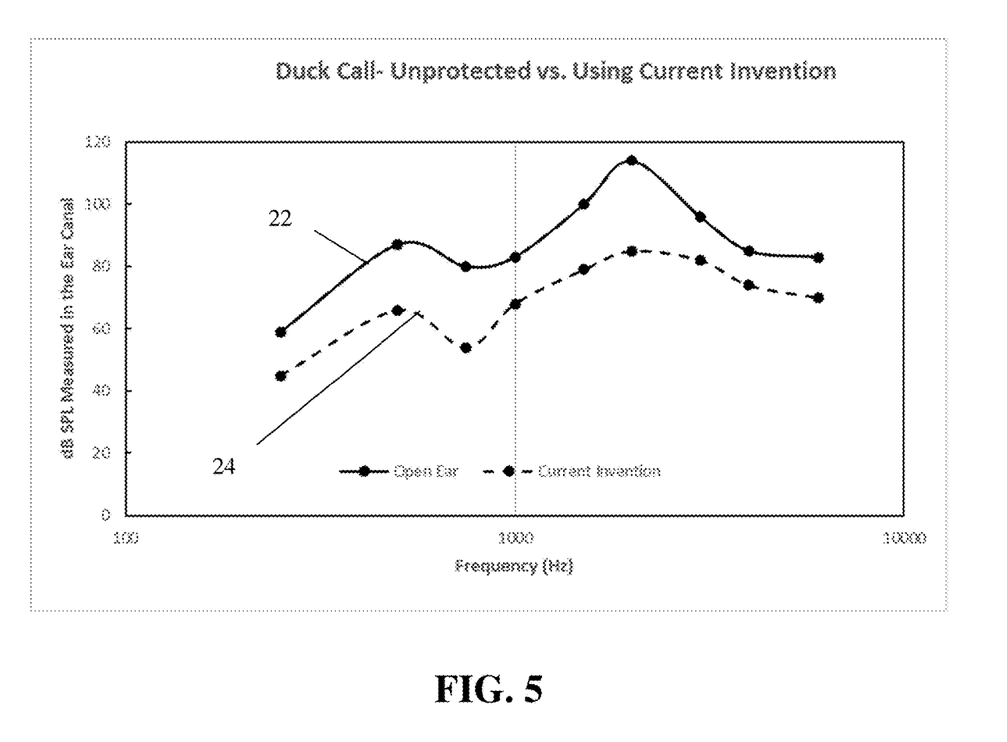
FIG. 5 is a plot of the frequency spectrum of an exemplary simulated game call made by a hunter being attenuated by a hearing device of the current disclosure.

Calling game requires the hunter/caller to produce sounds through a calling mechanism and make adjustments to the volume, pitch, and cadence. Many types of calls (duck, goose, turkey and elk diaphragm calls) are produced by the caller creating air turbulence across a diaphragm or reed, either in the caller's mouth or in the calling instrument. Much like human speaking, hearing is required to monitor the volume and accuracy of the sound. Traditional attenuation methods of hearing protection, such as standard ear plugs, both lower the volume of the calling, but also change the spectral characteristics. By plugging the ear and concha bowl of the ear, the natural resonance and gain characteristics of the human ear and canal are eliminated. This phenomenon is known as insertion loss. Insertion loss can distort the sound quality and frequency content of the signal. Using digital, multi-channel compression with gain applied to compensate for the insertion loss and suppress the high levels of the call while not reducing lower levels, the current invention can maintain the spectral characteristics of the calling apparatus while simultaneously reducing the high level outputs. FIG. 5 shows the output frequency spectrum measured in an unoccluded human ear of a duck call and the processed sound signal 24 produced with a hearing device of the present disclosure. With the hearing or listening device of the present disclosure, the spectral shape of the calling sound can be maintained, while the overall intensity or amplitude is lowered. So not only is the call attenuated, but the spectral frequency of the call sound being transferred to the ear canal via the processed sound signal 24 is maintained.

In many instances, a call to be simulated by a hunter will have a similar spectral frequency as that made by an animal being hunted, or the target sound signature. However, the simulated call being produced near the user's ear can have a harmful amplitude or intensity. In some embodiments, the sound processing unit 18 can be programmed to identify the target sound signature, which could be from either an animal being hunted or from a calling device of the hunter, and process the target sound signature differently based on the amplitude of the sound signature. If the amplitude of the target sound signature is below a predetermined minimum target sound amplitude, for instance from a distant animal, the sound can be amplified for the processed sound signal 24. If the amplitude of the target sound signature is above a predetermined target sound amplitude maximum, for instance when received from a call device and produced by the user or a nearby hunter, the target sound signature can be attenuated to a safe level. As such, the device 10 can distinguish between target sound signatures having similar frequency spectrums based on amplitude and process such target sound signatures differently. This allows target sound signatures from distant animals to be amplified so the hunter can better hear such sound produced from the target animal, while reducing the target sound signatures from a call device to a safe level, but a level at which the target sound signature and spectral characteristics of the target sound signature from the call device can be maintained to help the hunter produce an accurate call. In other words, target sound signatures having a harmful amplitude can undergo flat and equal attenuation.

In some embodiments, the target sound signatures can be either amplified or attenuated by a preset decibel level. For instance all target sound signatures below a predetermined amplitude can be amplified by 20 decibels, and all target sound signatures above a predetermined maximum amplitude can be attenuated by 20 decibels. In other embodiments, the amount of amplification or attenuation produced for the target sound signature (or the undesirable sound signatures) can vary relative to the amplitude level. For instance, a target sound signature at 10 decibels can be amplified by 40 decibels and a target sound signature at 40 decibels can be amplified by 20 decibels. In this instance, target sounds can be amplified to a desired amplitude, which in some embodiments can be between 60 and 100 decibels, to provide target sounds at an amplitude that are safe and easy to hear. Similarly, target sound signatures being amplified can undergo flat and equal amplification such that the frequency spectrum of the target sound signature in the processed sound signal 24 can be substantially similar to the frequency spectrum of the target sound signature in the environmental sound signal 22.

A similar correlation could be programmed for target sound signatures (and undesirable sound signatures) having larger harmful amplitudes. For instance, a sound signature for a gunshot impulse at 160 decibels could be attenuated by 20 or more decibels to bring the gunshot impulse amplitude below a safe 140 decibel level, whereas a sound signature at 120 decibels for a turkey call or a loud shouting by a companion could be attenuated by 20 or more decibels to at or below 100 decibels to help ensure that different harmful sound signatures are sufficiently attenuated to safe levels depending on the sound at issue. In some embodiments, undesirable sounds above a maximum amplitude can reduced by a fixed amount, for instance 20 decibels. In other embodiments, the undesirable or harmful sounds could be reduced to a desired target amplitude, for instance a sound signature having either a 120 or a 110-decibel amplitude could be reduced to a 100-decibel amplitude. In some embodiments, the target sound signatures can be either amplified or attenuated to the same desired amplitude by the sound processing unit 18, such as a desired target amplitude between about 60 and 100 decibels.

The sound processing unit 18 can have a limiter such that any sound signals produced by the sound processing unit 18 could have a maximum amplitude, for instance 100 decibels.

In this instance, while the earpiece 12 itself may only be able to attenuate a loud sound by 20 decibels or so, such that a muffled harmful sound may still enter the ear canal through the earpiece medium, the sound processing unit 18 can also produce a processed sound signal 24 which includes a replicated or mimicked sound signal of the harmful or undesirable sound signature at a safe level. In a calling environment for instance, if a call is made with an amplitude of 130 decibels, that call sound can pass into the ear canal at an amplitude of around 110 decibels due to the attenuation of the earpiece 12 itself. The 110 decibel sound can be muffled similar to a call transferred in a conventional ear piece or earplug. Simultaneously, the sound processing unit 18 can transmit a replicated call sound signal via the sound processing unit 18 that can have a safe amplitude of 60-100 decibels. This same process can be applied to gun fire so that in addition to the gun shot being attenuated as much as possible via the earpiece 12, a replicated gunshot sound at a safe level can be projected to the user's ear canal so the user can clearly hear and locate the gunshot.

As such, in some embodiments, the sound processing unit 18 can be programmed to filter out harmful amplitudes which cannot be sufficiently reduced to a safe or desired level and reproduce a new sound signature mimicking that of the undesirable or harmful sound signature at an amplitude that is safe and easy to hear. That way the user can still receive the benefit of having a clear and safe sound signal for the undesirable or harmful sound signature as part of the processed sound signal as opposed to hearing only a distorted sound signal for that undesirable sound signature similar to conventional ear protection devices such as ear plugs.

In some embodiments, the sound processing unit 18 can be programmed to accommodate users of differing hearing capacities. For instance, a user with normal hearing may require less amplification for lower amplitude sounds and more attenuation for higher amplitude sounds than a person with damaged or impaired hearing. As such, audiograms or hearing profiles programmed into the sound processing unit 18 can be tailored or customized to the support the hearing level of the user in some embodiments, such that the device can both accommodate the user's individual hearing loss, as well as identify and enhance target sounds suitable for a particular hunting pursuit (e.g. turkey, elk, etc.) or other target sound signatures. This hearing enhancement to compensate for hearing loss can be done using flat attenuation, which can provide a benefit over conventional devices that normalize all sounds received by the microphone and projects all sounds at the same amplitude. By using flat equal amplification of background or environmental noises, the differences in amplitude levels between different background or environmental sounds can be preserved to maintain a similar hearing experience for the user as if no hearing device was being worn. Target sounds can be further amplified to highlight them within the environmental sound signal, and harmful or undesirable sounds can be suppressed as described herein.

Thus, although there have been described particular embodiments of the present invention of a new and useful Hearing Enhancement and Protection Device, it is not intended that such references be construed as limitations upon the scope of this invention.

What is claimed is:

1. A listening device for positioning in an ear canal of a user to process an environmental sound signal, the listening device comprising:

an earpiece, at least a portion of the earpiece shaped to at least partially occlude the ear canal of the user when the portion of the earpiece is positioned in the ear canal of the user;

a microphone positioned on the earpiece for receiving the environmental sound signal when the earpiece is positioned in the user's ear canal;

a sound processing unit electrically coupled to the microphone, the sound processing unit programmed to produce a processed sound signal by identifying a target sound signature within the environmental sound signal received from the microphone, and within the processed sound signal, amplify the identified target sound signature if the identified target sound signature has an amplitude below a predetermined target sound amplitude threshold, and attenuate the identified target sound signature if the amplitude of the identified target sound signature is above a predetermined target sound amplitude maximum; and a speaker electrically coupled to the sound processing unit, the speaker configured to project the processed sound signal as audible sound.

2. The device of claim 1, wherein the target sound signature has a frequency spectrum which corresponds to a turkey gobble.

3. The device of claim 1, wherein the target sound signature has a frequency spectrum which corresponds to an elk bugle.

4. The device of claim 1, wherein the target sound signature has a frequency spectrum which corresponds to one of the following: a mallard greeting call, a water fowl call, a deer call, or an upland game call.

5. The device of claim 1, wherein the sound processing unit can be programmed to identify one or more undesirable sound signatures from the environmental sound signal, the sound processing unit programmed to, within the processed sound signal, attenuate the one or more undesirable sound signatures in producing the processed sound signal.

6. The device of claim 5, wherein the undesirable sound signature includes a frequency spectrum and amplitude which corresponds to a gunshot.

7. The device of claim 5, wherein the sound processing unit is programmed to reproduce the undesirable sound signature within the processed sound signal at an amplitude of less than about 120 decibels.

8. The device of claim 1, wherein the predetermined maximum target sound amplitude is between about 110 and 140 decibels.

9. The device of claim 1, wherein the target sound signature is either amplified or attenuated to a desired target sound amplitude by the sound processing unit within the processed sound signal.

10. The device of claim 9, wherein the desired target sound amplitude is between about 60 and 100 decibels.

11. The device of claim 1, wherein background sound signatures having an amplitude less than a predetermined background sound amplitude maximum in the environmental sound signal are reproduced within the processed sound signal in an unaltered form.

12. The device of claim 1, wherein all background sound signatures having an amplitude less than a predetermined background sound amplitude maximum in the environmental sound signal are reproduced within the processed sound signal and subject to flat attenuation to compensate for hearing loss.

13. The device of claim 1, wherein the sound processing unit is programmed to identify multiple target sound signatures within the environmental sound signal, and the sound processing unit can be selectively alternated between amplifying one of the multiple target sound signatures.

14. The device of claim 1, wherein the at least a portion of the ear piece that is positionable in the user's ear canal is shaped to fully occlude the user's ear canal when positioned within the user's ear canal.

15. The device of claim 14, wherein the at least a portion of the earpiece is configured to attenuate the environmental sound signal in its entirety by up to about 20 decibels when the at least a portion of the earpiece fully occludes the user's ear canal.

16. A listening device for positioning in an ear canal of a user to process an environmental sound signal, the listening device comprising:

an earpiece, at least a portion of the earpiece shaped to fully occlude the ear canal of the user when the portion of the earpiece is positioned in the ear canal of the user;

a microphone positioned on the earpiece for receiving the environmental sound signal when the earpiece is positioned in the user's ear canal;

a sound processing unit electrically coupled to the microphone, the sound processing unit programmed to identify at least one target sound signature within the environmental sound signal received from the microphone and produce a processed sound signal, wherein producing the processed sound signal includes:

amplifying the at least one identified target sound signature if the identified target sound signature has an amplitude below a predetermined amplitude threshold;

attenuating the at least one identified target sound signature if the amplitude of the identified target sound signature is above a predetermined target sound amplitude maximum;

passing through substantially all background sound signatures in the environmental sound signal having an amplitude less than a predetermined background sound amplitude maximum;

a speaker electrically coupled to the sound processing unit, the speaker configured to project the processed sound signal as audible sound.

17. The device of claim 16, wherein the sound processing unit is programmed to identify at least one undesirable sound signature in the environmental sound signal and attenuate the undesirable sound signature.

18. The device of claim 17, wherein the processed sound signal includes the undesirable sound signature at a lower amplitude than the amplitude of the undesirable sound signature of the environmental sound signal.

19. A method of processing an environmental sound signal; the method comprising the steps of:

providing a listening device having an earpiece, a microphone positioned on the earpiece, a sound processing unit communicated with the microphone, and a speaker communicated with the sound processing unit;

placing the earpiece in the ear of a user with at least a portion of the earpiece positioned within the ear canal of the user;

receiving with the microphone the environmental sound signal;

processing the environmental sound signal with the sound processing unit to:

identify a target sound signature within the environmental sound signal;

amplify the at least one identified target sound signature if the identified target sound signature has an amplitude below a predetermined amplitude threshold; and attenuate the at least one identified target sound signature if the amplitude of the identified target sound signature is above a predetermined target sound amplitude maximum; and projecting the processed sound signal as an audible sound through a speaker on the ear piece into the ear canal of the user.

20. The method of claim 19, wherein the processing step further comprises:

passing through substantially all background sound signatures in the environmental sound signal having an amplitude less than a predetermined background sound amplitude maximum.

\* \* \* \* \*